United States Patent [19]

Ravichandran et al.

[11] Patent Number: 5,023,283
[45] Date of Patent: * Jun. 11, 1991

[54] N,N-BIS(ACYLOXYETHYL)HYDROXYLAMINE DERIVATIVES

[75] Inventors: Ramanathan Ravichandran, Yonkers; Raymond Seltzer, New City, both of N.Y.

[73] Assignee: Ciba-Geigy Corporation, Ardsley, N.Y.

[*] Notice: The portion of the term of this patent subsequent to Jan. 19, 2005 has been disclaimed.

[21] Appl. No.: 344,559

[22] Filed: Apr. 25, 1989

Related U.S. Application Data

[63] Continuation of Ser. No. 946,222, Dec. 24, 1986, abandoned.

[51] Int. Cl.$^5$ .............................................. C07C 239/14
[52] U.S. Cl. .................................... 524/101; 524/100; 524/139; 524/189; 524/217; 524/222; 524/238; 523/455; 523/508; 252/51.5 A; 106/181; 260/404
[58] Field of Search ............... 524/100, 101, 139, 189, 524/217, 222, 238; 523/508, 455; 106/181; 252/51.5 A; 260/404

[56] References Cited

U.S. PATENT DOCUMENTS

| Re. 21,530 | 8/1940 | Kritchevsky | 260/404 |
| 2,176,703 | 10/1939 | De Groote et al. | 260/404 X |
| 2,371,429 | 3/1945 | De Groote et al. | 260/404 |
| 3,457,286 | 7/1967 | Dexter et al. | 260/404 |
| 3,644,278 | 2/1972 | Klemchuk | 260/45.8 |
| 4,277,319 | 7/1981 | Nyi et al. | 204/159.23 |
| 4,627,939 | 12/1986 | Moore et al. | 260/404 |
| 4,720,517 | 1/1988 | Ravichandran et al. | 524/101 |

FOREIGN PATENT DOCUMENTS 1001098  8/1965  United Kingdom ............... 260/45.8

Primary Examiner—Floyd D. Higel
Attorney, Agent, or Firm—Harry Falber

[57] ABSTRACT

Esters of N,N-bis(hydroxyethyl)hydroxylamines corresponding to the formula

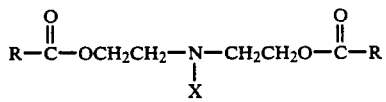

wherein R are various aliphatic and aromatic groups, and X is hydroxy or substituted carboxyethyl are effective in stabilizing various organic materials against oxidative, thermal and actinic degradation.

13 Claims, No Drawings

N,N-BIS(ACYLOXYETHYL)HYDROXYLAMINE DERIVATIVES

This application is a continuation of application Ser. No. 946,222, filed Dec. 24, 1986, now abandoned.

Organic polymeric materials such as plastics and resins are subject to thermal, oxidative and photodegradation. A great variety of stabilizers are known in the art for stabilizing a diversity of substrates. Their effectiveness varies depending upon the causes of degradation and the substrate stabilized. In general, it is difficult to predict which stabilizer will be most effective and most economical for any one area of application. For example, stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered.

Various organic hydroxylamine compounds are generally known and some are commercially available. A number of patents disclose nitrogen-substituted hydroxylamines as antioxidant stabilizers for various substrates including polyolefins, polyesters and polyurethanes. U.S. Pat. Nos. 3,432,578, 3,644,278, 3,778,464, 3,408,422, 3,926,909, 4,316,996, 4,386,224 and 4,590,231 are representative of such patents which basically disclose N,N-dialkyl-, N,N-diaryl and N,N-diaralkyl hydroxylamine compounds and their color improvement and color stabilizing activity. In addition, N-hydroxyimino acids and esters thereof are well known in the literature and have been indicated as biologically active. For example, N-hydroxyiminodiacetic acid is a commercially available compound. Representative publications disclosing such compounds include Kneifel and Bayer, J. Am. Chem. Soc. 108, 3075-77 (1986) which describes the stereochemistry and synthesis of a vanadium complex of N-(L-1-carboxyethyl)-N-hydroxy-L-alanine; Felcman et al, Inorg. Chem. Acta. 93, 101-8 (1984) which describes the synthesis and stability of several transition metal complexes of N-hydroxyiminodiacetic acid and the corresponding iminodi--propionic acid; and Japan Kokai 58,120,250 (1983) which describes a silver halide color developing solution containing a pyrrolidone polymer and hydroxyiminodiacetic acid. Polymer stabilization utility for these compounds is not mentioned.

It has now been determined that the compounds of this invention exhibit a variety of desirable stabilizing properties. Thus, the compounds serve to protect various substrates such as polyolefins, elastomers and lubricating oils against the adverse effects of oxidative and thermal degradation. They are most effective as lubricant stabilizers and as color improvers and process stabilizers in polyolefin compositions which may contain metal salts of fatty acids and which also contain a phenolic antioxidant. Thus, they serve to substantially reduce color formation resulting from the presence of the phenolic antioxidant and/or from the processing conditions as well as to directly protect the polymer from said processing conditions. They also prevent the discoloration of polyolefin compositions containing hindered amine light stabilizers or combinations of phenolic antioxidants and organic phosphites. In addition, the gas fading that may be experienced upon exposure to the combustion products of natural gas is also significantly reduced.

It is the primary object of this invention to provide a novel class of N,N-bis(hydroxyethyl)hydroxylamine esters which are effective stabilizers for a diverse group of organic materials.

It is another object of this invention to provide compositions of various organic materials stabilized against oxidative, thermal and actinic degradation by the presence therein of said esters.

It is a further object to provide such compositions which also contain phenolic antioxidants wherein said esters substantially reduce color formation resulting from the presence of said phenol.

Various other objects and advantages of this invention will become evident from the following description thereof.

The stabilizing compounds of this invention correspond to the formula

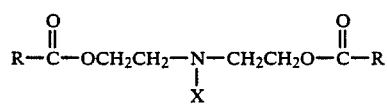

wherein each R is alkyl of 1 to 36 carbon atoms, cycloalkyl of 5 to 12 carbon atoms, phenyl, phenyl substituted by alkyl of 1 to 36 carbon atoms, aralkyl of 7 to 9 carbon atoms, said aralkyl substituted by alkyl of 1 to 36 carbon atoms, or

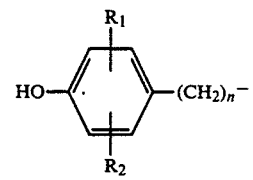

wherein $R_1$ and $R_2$ are independently alkyl of 1 to 18 carbon atoms, cycloalkyl of 5 to 12 carbon atoms, phenyl or aralkyl of 7 to 9 carbon atoms, and n is 0, 1 or 2; and X is hydroxyl or

wherein $R_3$ is alkyl of 1 to 36 carbon atoms, cycloalkyl of 5 to 12 carbon atoms, phenyl, phenyl substituted by alkyl of 1 to 36 carbon atoms, aralkyl of 7 to 9 carbon atoms or said aralkyl substituted by alkyl of 1 to 36 carbon atoms, and $R_4$ is hydrogen or methyl.

The R groups are preferably straight-chain or branched alkyl of 1 to 18 carbon atoms, such as methyl, n-butyl, tert.butyl, n-octyl, 2-ethylhexyl, decyl, dodecyl and octadecyl. Cycloalkyl is preferably cyclopentyl and cyclohexyl. Aralkyl is preferably benzyl, α-methylbenzyl or α,α-dimethylbenzyl. R is also preferably the 4-hydroxyphenyl group wherein $R_1$ and $R_2$ are in the ortho position to the hydroxyl group and are alkyl of 4 to 8 carbon atoms, and most preferably tert.butyl. X is preferably the hydroxyl group or

wherein $R_3$ is alkyl of 1 to 18 carbon atoms.

The compounds can be prepared by (1) reacting diethanolamine with the appropriately substituted acrylate or methacrylate $[CH_2=C(R_4)—COOR_3]$ at a temperature ranging from 25° to 200° C. to prepare the N-substituted diethanolamine starting product and (2) reacting said N-substituted diethanolamine with RCOCl in a solvent such as methylene chloride and in the presence of a proton acceptor such as a tertiary amine like triethylamine or pyridine, at a temperature ranging from 25° to 80° C. The resulting product reflects X as the

group.

In order to prepare the hydroxylamine product, i.e. X=OH, the product resulting from step (2) is reacted with an oxidizing agent such as m-chloroperoxybenzoic acid, in a solvent such as methylene chloride at a temperature ranging from 0° to 35° C.

The various reactants are commercially available or can be prepared by known methods. For example, the latter formation of the hydroxylamine derivative proceeds according to the reaction described in Cope et al, Organic Reactions 11, Chapter 5, 317 (1960).

The compounds are particularly effective in stabilizing organic materials such as plastics, polymers and resins in addition to mineral and synthetic fluids such as lubricating oils, circulating oils, etc.

Substrates in which the compounds are particularly useful are polyolefins such as polyethylene and polypropylene, polystyrene, including impact polystyrene, ABS resin, SBR, styrene/butadiene block copolymer, isoprene, as well as natural rubber, polyesters including polyethylene terephthalate and polybutylene terephthalate, including copolymers, polyphenylene oxide and lubricating oils such as those derived from mineral oil.

In general polymers which can be stabilized include
1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.
2. Mixtures of the polymers mentioned under 1), for example mixtures of polypropylene with polyisobutylene.
3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.
4. Polystyrene, poly-(p-methylstyrene).
5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.
6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA-or AES-polymers.
7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.
8. Polymers which are derived from $\alpha,\beta$-unsaturated acids and derivatives thereof, such as polyacrylates and polymethacrylates, polyacrylamide and polyacrylonitrile.
9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.
10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.
11. Homopolymers and copolymers of cyclic ethers, such as polyalkylene glycols, polyethylene oxide, polypropylene oxide or copolymers thereof with bis-glycidyl ethers.
12. Polyacetals, such as polyoxymethylene and those polyoxymethylenes which contain ethylene oxide as comonomer.
13. Polyphenylene oxides and sulfides, and mixtures of polyphenylene oxides with polystyrene.
14. Polyurethanes which are derived from polyethers, polyesters or polybutadiens with terminal hydroxyl groups on the one side and aliphatic or aromatic polyisocyanates on the other side, as well as precursors thereof (polyisocyanates, polyols or prepolymers).
15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.
17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.
18. Polycarbonates.
19. Polysulfones, polyethersulfones and polyetherketones.
20. Crosslinked polymers which are derived from aldehydes on the one hand and phenols, ureas and melamines on the other hand, such as phenol/formaldehyde resins, urea/formaldehyde resins and melamine/formaldehyde resins.
21. Drying and non-drying alkyd resins.
22. Unsaturated polyester resins which are derived from copolyesters of saturated and unsaturated dicarboxylic acids with polyhydric alcohols and vinyl compounds as crosslinking agents, and also halogen-containing modifications thereof of low flammability.
23. Thermosetting acrylic resins, derived from substituted acrylic esters, such as epoxy-acrylates, urethane-acrylates or polyester acrylates.
24. Alkyd resins, polyester resins or acrylate resins in admixture with melamine resins, urea resins, polyisocyanates or epoxide resins as crosslinking agents.
25. Crosslinked epoxide resins which are derived from polyepoxides, for example from bis-glycidyl ethers or from cycloaliphatic diepoxides.
26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methylcellulose.
27. Mixtures of polymers as mentioned above, for example PP/EPDM, Polyamide 6/EPDM or ABS, PVC/EVA, PVC/ABS, PVC/MBS, PC/ABS, PBTP/ABS.
28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.
29. Aqueous emulsions of natural or synthetic rubber, e.g. natural latex or latices of carboxylated styrene/butadiene copolymers.

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants 1.1. Alkylated monophenols, for example,
2,6-di-tert.butyl-4-methylphenol
2-tert.butyl-4,6-dimethylphenol
2,6-di-tert.butyl-4-ethylphenol
2,6-di-tert.butyl-4-n-butylphenol
2,6-di-tert.butyl-4-i-butylphenol
2,6-di-cyclopentyl-4-methylphenol
2-($\alpha$-methylcyclohexyl)-4,6-dimethylphenol
2,6-di-octadecyl-4-methylphenol
2,4,6-tri-cyclohexylphenol
2,6-di-tert.butyl-4-methoxymethylphenol 1.2. Alkylated hydroquinones, for example,
2,6-di-tert.butyl-4-methoxyphenol
2,5-di-tert.butyl-hydroquinone
2,5-di-tert.amyl-hydroquinone
2,6-diphenyl-4-octadecyloxyphenol 1.3. Hydroxylated thiodiphenyl ethers, for example
2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)

1.4. Alkylidene-bisphenols, for example,
2,2'-methylene-bis-(6-tert.butyl-4-methylphenol)
2,2'-methylene-bis-(6-tert.butyl-4-ethylphenol)
2,2'-methylene-bis-[4-methyl-6-($\alpha$-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-($\alpha$-methylbenzyl)-4-nonylphenol]
2,2'-methylene-bis-[6-($\alpha,\alpha$-dimethylbenzyl)-4-nonylphenol]
2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylphenyl-butane
2,6-di-(3-tert.butyl-5-methyl-2-hydroxybenzyl)-4-methylphenol
1,1,3-tris-(5-tert.butyl-4-hydroxy-2-methylphenyl)-butane
1,1-bis-(5-tert.butyl-4-hydroxy-2-methylphenyl)-3-n-dodecylmercaptobutane
ethylenglycol-bis-[3,3-bis-(3'tert.butyl-4'-hydroxyphenyl)-butyrate]
di-(3-tert.butyl-4-hydroxy-5-methylphenyl)-dicyclopentadiene
di-[2-(3'-tert.butyl-2'-hydroxy-5'-methyl-benzyl)-6-tert.butyl-4-methylphenyl]-terephthalate.

1.5. Benzyl compounds, for example, 1,3,5-tri-(3,5-di-tert.butyl-4-hydroxybenzyl)-2,4,6-trimethylbenzene-di-(3,5-di-tert.butyl-4-hydroxybenzyl)sulfide 3,5-di-tert.butyl-4-hydroxybenzyl-mercapto-acetic acid isooctyl ester bis-(4-tert.butyl-3-hydroxy-2,6-dimethylbenzyl)dithiol-terephthalate 1,3,5-tris-(3,5-di-tert.butyl-4-hydroxybenzyl)-isocyanurate 1,3,5-tris-(4-tert.butyl-3-hydroxy-2,6-dimethylbenzyl)isocyanurate 3,5-di-tert.butyl-4-hydroxybenzyl-phosphoric acid-dioctadecyl ester 3,5-di-tert.butyl-4-hydroxybenzyl-phosphoric acid-monoethyl ester, calcium-salt 1.6. Acylaminophenols, for example,
4-hydroxy-lauric acid anilide
4-hydroxy-stearic acid anilide
2,4-bis-octylmercapto-6-(3,5-tert.butyl-4-hydroxyanilino)-s-triazine
octyl-N-(3,5-di-tert.butyl-4-hydroxyphenyl)-carbamate 1.7. Esters of β-(3,5-di-tert-butyl-4-hydroxyphenyl)-propionic acid with monohydric or polyhydric alcohols, for example,

| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.8. Esters of β-(5-tert-butyl-4-hydroxy-3-methylphenyl)propionic acid with monohydric or polyhydric alcohols, for example,

| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.9. Amides of β-(3,5-di-tert.butyl-4-hydroxyphenyl)-propionic acid for example,
N,N'-di-(3,5-di-tert.butyl-4-hydroxyphenylpropionyl)-hexamethylenediamine
N,N'-di-(3,5-di-tert.butyl-4-hydroxyphenylpropionyl)-trimethylenediamine
N,N'-di-(3,5-di-tert.butyl-4-hydroxyphenylpropionyl)-hydrazine 2. UV absorbers and light stabilizers 2.1. 2-(2'-Hydroxyphenyl)-benzotriazoles, for example, the 5'-methyl-, 3',5'-di-tert.butyl-, 5'-tert.butyl-, 5'-(1,1,3,3-tetramethylbutyl)-, 5-chloro-3',5'-di-tert.butyl-, 5-chloro-3'-tert.butyl-5'-methyl-, 3'-sec.butyl-5'-tert.butyl-, 4'-octoxy, 3',5'-di-tert.amyl-, 3',5'-bis-(α,α-dimethylbenzyl)-derivative.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivative.

2.3. Esters of optionally substituted benzoic acids for example, phenyl salicylate, 4-tert.butyl-phenylsalicylate, octylphenyl salicylate, dibenzoylresorcinol, bis-(4-tert.butylbenzoyl)-resorcinol, benzoylresorcinol, 3,5-di-tert.butyl-4-hydroxybenzoic acid 2,4-di-tert-butyl-phenyl ester and 3,5-di-tert.butyl-4-hydroxybenzoic acid hexadecyl ester.

2.4. Acrylates, for example, α-cyano-β,β-diphenylacrylic acid ethyl ester or isooctyl ester, α-carbomethoxycinnamic acid methyl ester, α-cyano-β-methyl-p-methoxy-cinnamic acid methyl ester or butyl ester, α-carbomethoxy-p-methoxycinnamic acid methyl ester, N-(α-carbomethoxy-α-cyanovinyl)-2-methylindoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel dibutyldithiocarbamate, nickel salts of 4-hydroxy-3,5-di-tert.butylbenzylphosphonic acid monoalkyl esters, such as of the methyl, ethyl or butyl ester, nickel complexes of ketoximes such as of 2-hydroxy-4-methylphenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl)-sebacate, bis-(1,2,2,6,6-pentamethylpiperidyl)-sebacate, n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert.octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethylpiperazinone).

2.7. Oxalic acid diamides, for example, 4,4'-di-octylosyoxanilide, 2,2'-di-octyloxy-5,5'-di-tert.butyl-oxanilide, 2,2'-di-dodecyloxy-5,5'-di-tert.butyl-oxanilide, 2-ethoxy-2'-ethyl-oxanilide, N,N'-bis (3-dimethylaminopropyl)oxalamide, 2-ethoxy-5-tert.butyl-2'-ethyloxanilide and its mixture with 2-ethoxy-2'-ethyl-5,4'-di-tert.butyloxanilide and mixtures of ortho- and para-methoxy-as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert.butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearyl-pentaerythrit diphosphite, tris-(2,4-di-tert.butylphenyl) phosphite, di-isodecylpentaerythritol diphosphite, di-(2,4-di-tert.-butylphenyl)pentaerythritol diphosphite, tristearylsorbitol triphosphite, tetrakis-(2,4-di-tert.butylphenyl)-4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythritol-tetrakis-(β-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.
8. Nucleating agents, for example, 4-tert.butyl-benzoic acid, adipic acid, diphenylacetic acid.
9. Fillers and reinforcing agents, for example, calcium carbonate, silicates, glass fibers, asbestos, talc, kaolin, mica, barium sulfate, metal oxides and hydroxides, carbon black, graphite.
10. Other additives, for example, plasticizers, lubricants, emulsifiers, pigments, optical brighteners, flame-proofing agents, anti-static agents, blowing agents and thiosynergists such as dilaurylthiodipropionate or distearylthiodipropionate.

While the instant compounds can be beneficially used as stabilizers for a variety of substrates, particularly the polyolefins, both alone and in conjunction with other coadditives, the introduction of the instant compounds into polyolefins, optionally containing various alkali metal, alkaline earth metal and aluminum salts of higher fatty acids (see Additive #7 hereinabove), with hindered phenolic antioxidants results in enhanced and particularly salubrious protection to such substrates in terms of reducing color formation stemming from the presence of the phenols. Such phenolic antioxidants include n-octadecyl 3,5-di-tert-butyl-4-hydroxyhydrocinnamate, neopentanetetrayl tetrakis-(3,5-di-tert-butyl-4-hydroxyl-hydrocinnamate), di-n-octadecyl 3,5-di-tert-butyl-4-hydroxybenzyl-phosphonate, 1,3,5-tris-(3,5-di-tert-butyl-4-hydroxy-benzyl)isocyanurate, thiodiethylene bis(3,5-di-tert-butyl-4-hydroxyhydrocinnamate), 1,3,5-trimethyl-2,4,6-tris (3,5-di-tert-butyl-4-hydroxybenzyl)benzene, 3,6-di-oxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-di-methyl-4-tert-butyl-3-hydroxybenzyl)isocyanurate, 1,1,3-tris-(2-methyl-4-hydroxy-5-tert-butylphenyl)butane, 1,3,5-tris-[2-(3,5-di-tert-butyl-4-hydroxyhydrocinnamoyloxy)-ethyl]-isocyanurate, 3,5-di-(3,5-di-tert-butyl-4-hydroxybenzyl)-mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl-3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-tert-butyl-4-hydroxyhydroxo-cinnamoyloxy)ethyl]-oxamide, and preferably neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris-(3,5-di-tert-butyl-4-hydroxybenzyl)isocyanurate, 2,6-di-tert-butyl-p-cresol or 2,2'-ethylidene-bis(4,6-di-tert-butylphenol).

Likewise, the instant compounds prevent color formation when hindered amine light stabilizers are present, such hindered amines including bis(1,2,2,6,6,-pentamethyl-4-piperidyl)-2-n-butyl-2-(3,5-di-tert-butyl-4-hydroxybenzyl) malonate; bis(2,2,6,6-tetramethyl-4-piperidyl) sebacate; dimethylsuccinate polymer with 4-hydroxy-2,2,6,6-tetramethyl-1-piperidinethanol; and polymer of 2,4-dichloro-6-octylamino-s-triazine with N'-(2,2,6,6-tetra-methyl-4-piperidyl)hexamethylene diamine.

The following examples illustrate the embodiments of this invention.

EXAMPLE I

N-[2-Methoxycarbonylethyl]diethanolamine starting product

A mixture of 10.5 grams of diethanolamine and 17.2 grams of methyl acrylate is heated under reflux for 24 hours. The excess methyl acrylate is removed under reduced pressure and the residue is purified using flash chromatography to afford the title compound as a thick oil.

EXAMPLE II

N,N-Bis[2,2'-stearoyloxyethyl]-N-[2-methoxycarbonylethyl]amine

A solution of 6.7 grams of the compound of Example I in 50 ml of methylene chloride containing 9.8 ml of triethylamine is added dropwise to a solution of 21.22 grams of stearoyl chloride in 50 ml of methylene chloride, and the reaction mixture is stirred at room temperature for 12 hours. The precipitated triethylamine hydrochloride is removed by filtration and the filtrate is concentrated under reduced pressure. Purification of the residue by liquid chromatography affords the title compound as a white solid: m.p. 50°–52° C.

Anal. Calcd. for $C_{44}H_{85}NO_6$: C, 73.0; H, 11.8; N, 1.9. Found: C, 73.0; H, 12.1; N, 1.9.

EXAMPLE III

N,N-Bis[2,2'-stearoyloxyethyl]hydroxylamine

A solution of 6.0 grams of the compound of Example II in 25 ml of methylene chloride is added dropwise to a solution of 1.79 grams of meta-chloroperoxybenzoic acid (m-CpBA) in methylene chloride. After stirring the reaction mixture at room temperature overnight under $N_2$, the solvent is removed under reduced pressure. The resulting residue is dissolved in methylene chloride and successively washed with saturated aqueous $NaHSO_3$, saturated aqueous $NAHCO_3$, brine and dried and evaporated. The resulting residue is recrystallized from i-propanol to afford the title compound as a white crystalline solid: m.p. 72°–74° C.

Anal. Calcd. for $C_{40}H_{79}NO_5$: C, 73.5; H, 12.2; N, 2.1. Found: C, 73.1; H, 12.4; N, 2.0.

EXAMPLE IV

N,N-Bis[2,2'-acetoxyethyl]-N-[2-methoxycarbonylethyl]amine

The procedure of Example II is repeated using 5.0 grams of N-[2-methoxycarbonylethyl]diethanolamine, 3.7 ml of acetyl chloride and 7.3 ml of triethylamine in methylene chloride to afford the title compound as a yellow oil.

EXAMPLE V

N,N-Bis[2,2'-acetoxyethyl]hydroxylamine

The procedure of Example III is repeated using 1.47 grams of the compound of Example IV and 0.92 grams of m-CpBA in methylene chloride, to afford the title compound as a light yellow oil.

EXAMPLE VI

N,N-Bis[2,2'-(3,5-di-tert-butyl-4-hydroxyphenylpropionyl)oxyethyl]-N-[2-methoxycarbonylethyl]amine The procedure of Example II is repeated using 2.65 grams of N-(2-methoxycarbonylethyl)diethanolamine, 7.85 grams of 2-(3,5-di-tert-butyl-4-hydroxyphenyl)propionyl chloride and 3.9 ml of triethylamine in methylene chloride to afford the title compound as a light yellow oil.

Anal. Calcd. for $C_{42}H_{65}NO_8$: C, 70.9; H, 9.2; N, 2.0. Found: C, 70.1; H, 9.3; N, 2.1.

EXAMPLE VII

N,N-Bis[2,2'(3,5-di-tert-butyl-4-hydroxyphenylpropionyl)oxyethyl]hydroxylamine

The procedure of Example III is repeated using 6.05 grams of the compound of Example VI and 1.98 grams of m-CpBA in methylene chloride, to afford the title compound as a white solid: m.p. 107°–110° C.

Anal. Calcd. for $C_{38}H_{69}NO_7$: C, 71.1; H, 9.3; N, 2.2. Found: C, 71.3; H, 9.5; N, 2.2.

EXAMPLE VIII

N,N-Bis-[2,2'-(3,5-di-tert-butyl-4-hydroxybenzoyl)oxyethyl]-N-[2-methoxycarbonylethyl]amine The procedure of Example II is repeated using 5.37 grams of N-(2-methoxycarbonylethyl) diethanolamine, 10.75 grams of 3,5-di-tert-butyl-4-hydroxybenzoylchloride and 5.58 ml of triethylamine in methylene chloride to afford the title compound as a white foam.

Anal. Calcd. for $C_{38}H_{57}NO_8$: C, 69.6; H, 8.8; N, 2.1. Found: C, 69.9; H, 8.7; N, 1.9.

EXAMPLE IX

N,N-Bis-[2,2'-(3,5-di-tert-butyl-4-hydroxybenzoyl)oxyethyl]-hydroxylamine

The procedure of Example III is repeated using 9.32 grams of the compound of Example VIII and 3.06 grams of m-CpBA in methylene chloride to afford the title compound as a white solid: m.p. 151°–153° C.

Anal. Calcd. for $C_{34}H_{51}NO_7$: C, 69.7; H, 8.8; N, 2.4. Found: C, 70.1; H, 9.2; N, 2.4.

EXAMPLE X

Processing of Polypropylene

| Base Formulation | |
|---|---|
| Polypropylene* | 100 parts |
| Calcium Stearate | 0.10 part |

*Profax 6501 from Himont U.S.A.

Stabilizers are solvent blended into polypropylene as solutions in methylene chloride and after removal of solvent by evaporation at reduced pressure, the resins are extruded using the following extruder conditions:

| | Temperature (°C.) |
|---|---|
| Cylinder #1 | 232 |
| Cylinder #2 | 246 |
| Cylinder #3 | 260 |
| Gate #1 | 260 |
| Gate #2 | 260 |
| Gate #3 | 260 |

| | Temperature (°C.) |
|---|---|
| RPM | 100 |

The melt flow rate (MFR) is determined by ASTM method 1238 condition L. The melt flow rate is the measure of the molecular weight for a specific type of polymer. The results are shown below.

| Additive | MFR After Extrusion (g/10 min.) | |
|---|---|---|
| | 1 | 5 |
| Base Resin | 7.9 | 44.3 |
| 0.1% Antioxidant A | 5.3 | 8.7 |
| 0.1% Antioxidant A + 0.05% of Ex. III | 2.8 | 5.7 |

Antioxidant A - neopentyl tetrakis [3-(3',5'-di-tert.butyl-4'-hydroxyphenyl)propionate]

EXAMPLE XI

Stabilization of Polypropylene

Unstabilized polypropylene powder (Hercules Profax 6501) is thoroughly blended with the indicated amount of additive. The blended materials are then milled on a two-roll mill at 182° C. for five minutes, after which time the stabilized polypropylene is sheeted from the mill and allowed to cool. The milled polypropylene is then cut into pieces and compression molded on a hydraulic press at 250° C. and 175 psi ($1.2 \times 10_6$Pa) into 25 mil plaques. The samples are exposed in a fluorescent sunlight/black light chamber until failure. Failure is taken as the hours required to reach 0.5 carbonyl absorbance by infrared spectroscopy on the exposed films.

| Additive | Conc. (% by Weight) | FS/BL Test Results (Hours to Failure) |
|---|---|---|
| None | — | 100 |
| Example III | 0.2 | 370 |

The instant compounds are thus seen to be effective color and process stabilizers in polypropylene compositions.

Summarizing, it is seen that this invention provides a group of compounds having improved stabilizing activity in a variety of organic materials. Variations may be made in proportions, procedures and materials without departing from the scope of the invention as defined by the following claims.

What is claimed is:

1. A compound of the formula

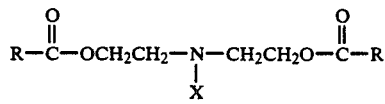

wherein each R is alkyl of 1 to 18 carbon atoms and X is hydroxyl.

2. N,N-Bis[2,2'-stearoyloxyethyl]hydroxylamine according to claim 1.

3. N,N-Bis[2,2'-acetoxyethyl]hydroxylamine according to claim 1.

4. A composition of matter consisting essentially of a plastic, polymer, resin or oil subject to oxidative, thermal and actinic degradation stabilized with an effective stabilizing amount of a compound of claim 1.

5. The composition of claim 4, wherein the polymer is a synthetic polymer.

6. The composition of claim 5, wherein the synthetic polymer is a polyolefin homopolymer or copolymer.

7. The composition of claim 6, which also contains an alkali metal, alkaline earth metal or aluminum salt of a higher fatty acid.

8. The composition of claim 4 which also contains a phenolic antioxidant.

9. The composition of claim 7 which also contains a phenolic antioxidant.

10. The composition of claim 9, wherein said phenolic antioxidant is selected from the group consisting of n-octadecyl 3,5-di-tert-butyl-4-hydroxyhydrocinnamate, neopentanetetrayl tetrakis-(3,5-di-tert-butyl-4-hydroxylhydrocinnamate), di-n-octadecyl 3,5-di-tert-butyl-4-hydroxybenzyl-phosphonate, 1,3,5-tris(3,5-di-tert-butyl-4-hydroxy-benzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-di-oxaoctamethylene bis(3-methyl-5-tert-butyl-4-hydroxyhydrocinnamate), 2,6-di-tert-butyl-p-cresol, 2,2′-ethylidene-bis(4,6-di-tert-butyl-phenol), 1,3,5-tris-(2,6-di-methyl-4-tert-butyl-3-hydroxybenzyl)isocyanurate, 1,1,3-tris-(2-methyl-4-hydroxy-5-tert-butylphenyl)butane, 1,3,5-tris-[2-(3,5-di-tert-butyl-4-hydroxyhydrocinnamoyloxy)-ethyl]-isocyanurate, 3,5-di-(3,5-di-tert-butyl-4-hydroxybenzyl)-mesitol, hexamethylene bis(3,5-di-tert-butyl-4-hydroxyhydrocinnamate), 1-(3,5-ditert-butyl-4-hydroxyanilino)-3,5-di(octylthio)-s-triazine, N,N′-hexamethylene-bis(3,5-di-tert-butyl-4-hydroxyhydrocinnamamide), calcium bis(ethyl-3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4hydroxyhydrocinnamoyl)hydrazide, and N,N′-bis[2-(3,5-tert-butyl-4-hydroxyhydroxocinnamoyloxy)-ethyl]-oxamide.

11. The composition of claim 10, wherein said phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl2,4,6-tris(3,5-di-tert-butyl-4-hydroxybenzyl)benzene, 1,3,5-tris-(3,5-di-tert-butyl-4-hydroxybenzyl)isocyanurate, 2,6-di-tert-butyl-p-cresol or 2,2′-ethylidene-bis(4,6-di-tertbutylphenol).

12. The composition of claim 4 which also contains antioxidants, benzotriazole UV absorbers, hindered amine light stabilizers, phosphites, thiosynergists or mixtures thereof.

13. A method for stabilizing a plastic, polymer, resin or oil against oxidative, thermal and actinic degradation which consists essentially of incorporating into said plastic, polymer, resin or oil an effective stabilizing amount of a compound of claim 1.

* * * * *